(12) United States Patent
Trogolo et al.

(10) Patent No.: US 7,357,949 B2
(45) Date of Patent: *Apr. 15, 2008

(54) ENCAPSULATED INORGANIC ANTIMICROBIAL ADDITIVE FOR CONTROLLED RELEASE

(75) Inventors: Jeffrey A. Trogolo, Boston, MA (US); Frank C. Rossitto, Danvers, MA (US); Edward K. Welch, II, Ipswich, MA (US)

(73) Assignee: Agion Technologies Inc., Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/032,372

(22) Filed: Dec. 21, 2001

(65) Prior Publication Data

US 2003/0118664 A1 Jun. 26, 2003

(51) Int. Cl.
*A61K 33/24* (2006.01)
*A61K 47/30* (2006.01)
*A01N 59/16* (2006.01)

(52) U.S. Cl. ............... 424/617; 424/618; 424/621; 424/630; 424/639; 424/641; 424/644; 424/646; 424/649; 424/651; 424/652; 424/653; 424/654; 424/655; 514/772.3

(58) Field of Classification Search ............... 424/405, 424/421, 497, 501, 618; 514/769, 770, 772.3, 514/772.4, 772.6, 951, 963, 965
See application file for complete search history.

(56) References Cited

U.S. PATENT DOCUMENTS

| | | | |
|---|---|---|---|
| 3,975,350 A * | 8/1976 | Hudgin et al. | 524/108 |
| 3,981,970 A * | 9/1976 | Wada et al. | 424/306 |
| 4,403,083 A * | 9/1983 | Marans et al. | 528/44 |
| 4,657,835 A | 4/1987 | Yashiki | |
| 4,775,585 A | 10/1988 | Hagiwara et al. | |
| 4,959,268 A | 9/1990 | Hagiwara et al. | |
| 5,096,958 A | 3/1992 | Meguro et al. | |
| 5,180,585 A | 1/1993 | Jacobson et al. | |
| 5,238,749 A | 8/1993 | Cueman et al. | |
| 5,305,827 A | 4/1994 | Steele et al. | |
| 5,376,411 A | 12/1994 | Nishishita | |
| 5,382,424 A * | 1/1995 | Stapler et al. | 424/54 |
| 5,527,854 A | 6/1996 | Matsukawa et al. | |
| 5,556,699 A * | 9/1996 | Niira et al. | 428/323 |
| 5,599,583 A * | 2/1997 | Lew et al. | 427/213.3 |
| 5,650,446 A | 7/1997 | Wellinghoff et al. | |
| 5,980,620 A | 11/1999 | Brodie et al. | |
| 6,013,275 A | 1/2000 | Konagaya et al. | |
| 6,046,243 A | 4/2000 | Wellinghoff et al. | |
| 6,093,407 A | 7/2000 | Cummings et al. | |
| 6,113,936 A * | 9/2000 | Takebayashi et al. | 424/419 |
| 6,123,925 A | 9/2000 | Barry et al. | 424/49 |
| 6,129,782 A | 10/2000 | Brodie et al. | |
| 6,156,245 A * | 12/2000 | Takebayashi et al. | 264/4.7 |
| 6,287,285 B1 | 9/2001 | Michal et al. | |
| 6,290,962 B1 | 9/2001 | Michetti et al. | |
| 6,296,834 B1 | 10/2001 | Bernard et al. | |
| 6,399,735 B1 * | 6/2002 | Fischer et al. | 528/76 |
| 6,413,536 B1 | 7/2002 | Gibson et al. | |
| 6,432,416 B1 | 8/2002 | Cummings et al. | |
| 6,436,422 B1 | 8/2002 | Trogolo et al. | |
| 2001/0009831 A1 | 7/2001 | Schink et al. | |
| 2003/0043341 A1 * | 3/2003 | Turner et al. | 351/160 R |

FOREIGN PATENT DOCUMENTS

| | | |
|---|---|---|
| EP | 0899024 A2 | 3/1999 |
| GB | 2297552 | 8/1996 |
| JP | 04066512 | 2/1992 |
| JP | 4066512 | 3/1992 |
| JP | 04066512 A * | 3/1992 |
| JP | 05154174 | 6/1993 |
| JP | 19940333532 | 12/1994 |
| JP | 8165210 | 6/1996 |
| JP | 08199089 A2 | 8/1996 |
| JP | 08217998 A2 | 8/1996 |
| JP | 19980023425 | 2/1998 |
| JP | 10316899 A2 | 12/1998 |
| JP | 11222402 A * | 8/1999 |
| JP | 2000028286 | 1/2000 |
| WO | WO 9413726 A1 * | 6/1994 |
| WO | WO97/46626 | 12/1997 |
| WO | WO 01/74166 A1 | 10/2001 |
| WO | WO 02/45953 A1 | 6/2002 |

OTHER PUBLICATIONS

STN online, file JICST-EPlus, Acc. No. 960462151 (Yukei et al., Bokin Bobai (Journal of Antibacterial and Antifungal Agents) (1996), vol. 24, No. 5, pp. 337-342), Abstract.*

* cited by examiner

*Primary Examiner*—Johann Richter
*Assistant Examiner*—Frank I. Choi
(74) *Attorney, Agent, or Firm*—IP & L Solutions; Edward K. Welch, II (57) ABSTRACT

The invention relates to a microcapsule comprising an inorganic antimicrobial agent coated with a hydrophilic polymer. The hydrophilic polymer is able to absorb sufficient water as to enable the action of the encapsulated antimicrobial agent. These microcapsules are useful to impart antimicrobial activity and can be used in polymer compositions, sprays and coatings. A method of preparing the microcapsule by treatment of the antimicrobial agent with a solution of the hydrophilic polymer is provided. Another embodiment of the invention is a method of preparing the microcapsule by coating of the antimicrobial agent with a polymer precursor followed by treatment with a reactive ingredient. Another embodiment of the invention is a method of preparing the microcapsule by melt compounding the antimicrobial agent with the hydrophilic polymer followed by grinding to the desired particle size. Polymer compositions comprising the microcapsules and a matrix polymer are also provided. Another embodiment of the invention is an article prepared from the polymer compositions comprising the microcapsules and a matrix polymer.

43 Claims, 2 Drawing Sheets

ENCAPSULATED INORGANIC ANTIMICROBIAL ADDITIVE FOR CONTROLLED RELEASE

FIELD OF THE INVENTION

This invention relates to antimicrobial agents that are encapsulated with a hydrophilic coating.

BACKGROUND OF THE INVENTION

A number of inorganic materials have been shown to possess antimicrobial activity. They include metal ions such as silver, copper, zinc, mercury, tin, lead, bismuth, cadmium, chromium and thallium ions. It is theorized that these antimicrobial metal ions exert their effects by disrupting respiration and electron transport systems upon absorption into bacterial or fungal cells. Antimicrobial metal ions of silver, copper, zinc, and gold, in particular, are considered safe for in vivo use. Antimicrobial silver ions are particularly useful for in vivo uses due to the fact that they have the highest ratio of efficacy to toxicity.

Antimicrobial zeolites can be prepared by replacing all or part of the ion-exchangeable ions in zeolite with antimicrobial metal ions, as described in U.S. Pat. Nos. 4,911,898; 4,911,899; 4,938,955; 4,906,464; and 4,775,585.

Zirconium compounds, such as zirconium phosphates, have also been modified to provide antimicrobial characteristics, as described in U.S. Pat. Nos. 4,025,608 and 4,059,679. J. Antibact. Antifung. Agents Vol. 22, No. 10, pp. 595-601, 1994 and references therein describe the antimicrobial characteristics of zirconium phosphate ceramics.

Antimicrobial water soluble glasses have been used and are described in U.S. Pat. No. 5,470,585.

Antimicrobial hydroxyapatite powders have been prepared and are described in U.S. Pat. Nos. 5,009,898 and 5,268,174.

U.S. Pat. No. 4,775,585 discloses incorporating metal-zeolite into a polymer to obtain a polymer with bactericidal activity. U.S. Pat. No. 4,923,450 discloses incorporating zeolite in bulk materials for production of medical tubes. Dependent upon material selection and processing conditions, when zeolite is conventionally compounded into polymers, the zeolite often agglomerates, causing poor dispersion of the zeolite in the polymer. When such material is molded or extruded, the surface of the polymer is frequently beaded instead of flat. Poor dispersion of the zeolite also can cause changes in the bulk properties of the polymer, such as a reduction in tensile strength.

Furthermore, it has been found by the present inventors that conventionally compounding antimicrobial zeolites in many polymeric materials, dependent upon processing conditions and the particular polymer, can result in discoloration. This appears also to result from inadequate dispersion of the zeolite, i.e., the formation of zeolite aggregates in the material as well as from chemical reactions involving the antimicrobial metal ions and the polymer itself, e.g., additives, contaminants, residual catalysts, moisture, etc. in the polymer, and/or any air or water introduced during the compounding process.

In certain instances, these problems can be avoided by use of antimicrobial coatings. However, this requires an extra processing step and raises additional problems such as adherence and permanence of the coating.

U.S. Pat. No. 5,094,847 recognizes that in order to get the desired antibacterial activity, a large amount of zeolite powder must be added to the polyolefin resin and that this is accompanied by poorer appearance, lower physical properties and roughened surface appearance. They disclose using low levels of antimicrobial agent followed by a corona discharge treatment. This requires additional equipment and an extra processing step.

U.S. Pat. No. 5,614,568 discloses an antibacterial resin composition comprising a styrene resin, an antibacterial agent and a compound or polymer having at least one functional group and a molecular weight of 300 to 10,000. In order to obtain good antimicrobial activity, they require the use of low molecular weight compounds or low molecular weight polymers, which can have deleterious effects on properties.

U.S. Pat. No. 6,013,275 discloses a copolymer of an antibacterial agent and a hydrophilic substance. Copolymerization is an extra step, which adds to complexity and cost and limits the choice of both the hydrophilic substance and the antibacterial agent. The hydrophilic substance must have functional groups capable of reacting with and copolymerizing with the antibacterial agent. Similarly, the antibacterial agent must have reactive groups capable of forming a copolymer with the antibacterial agent.

WO 00/30697 discloses an antimicrobial coated substrate comprising an antimicrobial coating composition coated on a substrate. The antimicrobial coating composition comprises a hydrophilic polymer having antimicrobial ceramic particles dispersed therein. They require a coating process. This requires additional equipment and an extra processing step.

One of the problems in the prior art is the unavailability, for the most part, of that quantity of the antimicrobial agent which lies beneath the surface of the article or coating into which it is incorporated. Unless the antimicrobial agent migrates from the polymer matrix, a characteristic not common to inorganic, especially ion-exchange type, antimicrobial agents, the entombed antimicrobial agent is without utility or efficacy. This requires the use of a larger quantity of antimicrobial agents so as to provide a higher concentration at the surface, which is more costly and often imparts deleterious properties. There remains a need to provide an antimicrobial agent in a form that is suitable to impart antimicrobial properties without the accompanying problems of the prior art.

Another problem in the prior art is that while the use of hydrophilic coatings and polymer matrices may mitigate, at least in part, the foregoing problem, this beneficial improvement is limited to utility in the narrow class of hydrophilic coatings and polymers and, more importantly, the very limited end use applications for which such hydrophilic coatings and polymers are appropriate. Thus, there is also a need in the art to find a means by which antimicrobial agent entombed within a polymer coating or matrix can be accessed or available for providing antimicrobial efficacy regardless of polymer comprising the coating or matrix.

Yet another problem in the prior art is that the rate of release of the antimicrobial agent is determined by solubility of the antimicrobial agent or, in the case of the ion-exchange type antimicrobial agents, the ion-exchange rate of the ceramic carrier and the water exposure or flow across the surface containing the antimicrobial agent. In high moisture, especially high flow environments, for example, a dishwasher interior, a high solubility or ion-exchange rate may lead to a premature depletion of the antimicrobial agent; thus, greatly reducing the life time of the antimicrobial efficacy. Thus, there is also a need in the art to be able to control the release rate of the antimicrobial agent.

SUMMARY OF THE INVENTION

This invention provides for microcapsules. These microcapsules comprise an antimicrobial agent, typically in the form of a particle or particles, encapsulated within a hydrophilic polymer. The hydrophilic polymer is able to absorb sufficient water as to enable the action of the encapsulated antimicrobial agent. These microcapsules are useful to impart antimicrobial activity and can be used in polymer compositions, sprays and coatings.

Also a method is provided for preparation of the microcapsule. The antimicrobial agent is dispersed in a solution of the hydrophilic polymer and the mixture is added to an antisolvent to precipitate the hydrophilic polymer in the form of a microcapsule.

In another embodiment, the microcapsule is prepared by reaction of monomers containing a dispersion of the antimicrobial agent.

Another embodiment of the invention provides for the preparation of the microcapsules by compounding of the antimicrobial agent with the hydrophilic polymer and subsequent grinding of the compounded product to the desired particle size.

Yet another embodiment of the invention provides for antimicrobial polymer compositions prepared from the microcapsules. These compositions are suitable for use as, for example, molding compositions or in coatings. Articles are prepared from or treated with, respectively, these compositions.

BRIEF DESCRIPTION OF THE DRAWINGS

Each of FIGS. 1-3 depicts a cross-sectional view of a piece of cut polymer sheet. Each depiction presumes a similar concentration and, in the case of FIGS. 1 and 2, dispersion of the antimicrobial particles.

DETAILED DESCRIPTION OF THE INVENTION

All patent applications, patents, patent publications, and literature references cited in this specification are hereby incorporated by reference in their entirety. In the case of inconsistencies, the present description, including definitions, is intended to control.

According to the present invention, an antimicrobial agent is encapsulated with a hydrophilic polymer to form a microcapsule. While not wanting to be bound by theory, we believe that the encapsulating polymer enables good dispersion of the particle and prevents agglomeration of the antimicrobial agent. Lack of good dispersion necessitates higher loading to impart antimicrobial activity and causes deleterious effects such as poor appearance or decreased physical properties. We believe that the hydrophilic polymer can absorb sufficient water so as to allow slow transport of the metal ion through the encapsulating polymer layer. Consequently, essentially all of the encapsulated antimicrobial agent in microcapsules touching the surface is available to be transported through the hydrophilic polymer to impart antimicrobial activity. Without this encapsulation, except in the case of hydrophilic coatings and polymers, only the antimicrobial particles at the surface are available to impart activity.

Additionally, the use of encapsulated antimicrobial agents according to the present invention allows one to regulate, to a large extent, the rate of release of the antimicrobial agent. Generally, the rate of release increases as the water absorption of the hydrophilic polymer increases. When used in hydrophilic coatings and polymers, the use of antimicrobial agents, especially encapsulated antimicrobial agents, allows one to regulate the overall release rate through the polymer coating or matrix. Thus, while a highly hydrophilic polymer matrix would allow for fast water transmission, a lesser hydrophilic polymer used to encapsulate the antimicrobial agent would slow the release of the antimicrobial agent.

Figure 1:
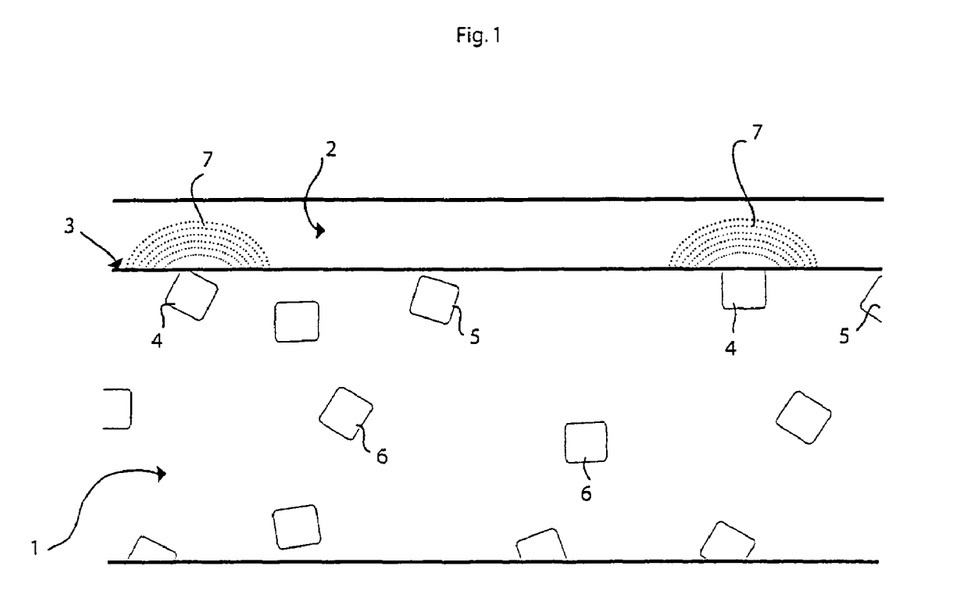
FIG. 1 represents the prior art wherein the antimicrobial particles are dispersed throughout a non-hydrophilic polymer matrix.

Again, while not wanting to be bound by theory, our understanding can be illustrated by reference to FIGS. 1-3. FIG. 1 represents the prior art system. The non-hydrophilic polymer matrix (1) has dispersed therein multiple particles of the antimicrobial agent (4, 5 and 6). Only those particles (4) which touch or protrude through the surface (3) are able to release the antimicrobial agent or active (7) into the water film (2). Antimicrobial particles entombed within the polymer matrix (5 and 6), including those close to the surface (5), are incapable of releasing the antimicrobial active since there is no diffusion path to the surface. If water could diffuse through the polymer matrix, it could reach the subsurface particles and access the antimicrobial there. Thus, despite the large deposit of antimicrobial agent in the polymer matrix, the source of efficacious antimicrobial agent is essentially limited to the surface layer of particles having a depth defined by the diameter of the particles. The diffusion kinetics out of those particles is defined by the particle structure, which cannot be altered. The prior art system has no flexibility with regard to source or kinetics, the only parameters we might control.

Figure 2:
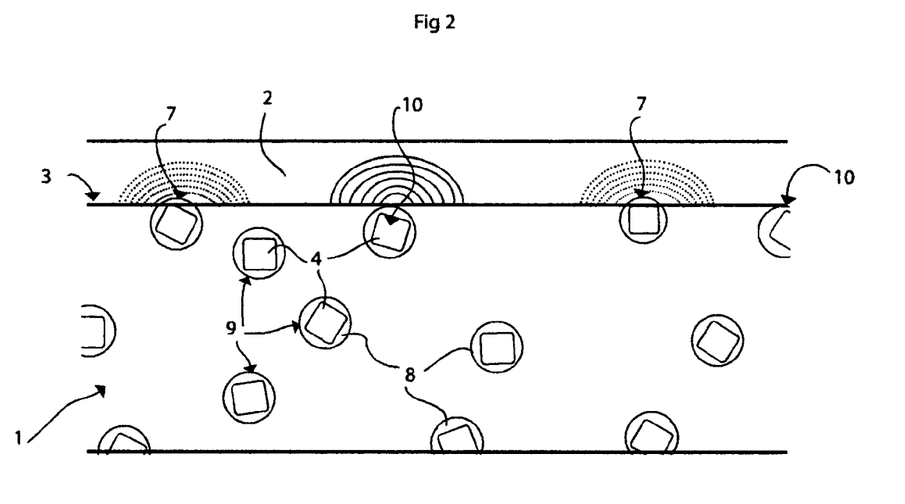
FIG. 2 represents one embodiment of the present invention wherein the individual antimicrobial particles are encapsulated.

FIG. 2 depicts the same matrix and particle dispersion as in FIG. 1 except here one embodiment of the present invention is illustrated wherein the individual antimicrobial particles are coated or encased within a hydrophilic polymer (8) to form microcapsules (9 and 10). The hydrophilic polymer coating essentially increases the effective diameter of the antimicrobial particles. Thus, whereas particles near the surface (5) in FIG. 1 were not capable of releasing antimicrobial agent, like encapsulated particles (10) in FIG. 2 are. In the depiction shown in FIG. 2, the amount and rate of release of the antimicrobial agent from the defined surface area would be about twice that of FIG. 1, depending upon the diffusion rate through the hydrophilic coating.

Figure 3:
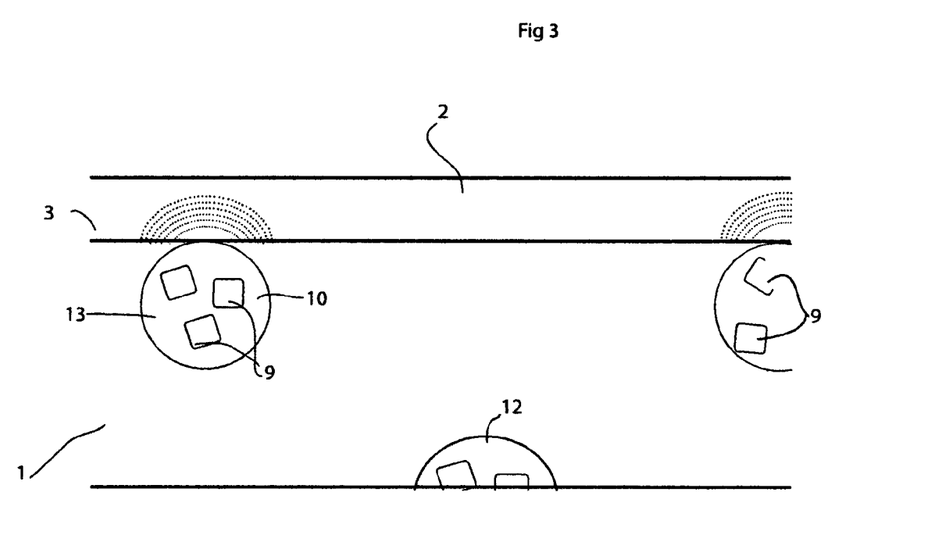
FIG. 3 represents one embodiment of the present invention wherein multiple particles of the antimicrobial agent are encapsulated in the same microcapsule.

FIG. 3 depicts yet another embodiment of the present invention wherein multiple antimicrobial particles (4) are contained in a single hydrophilic capsule (11, 12) resulting in particle clusters within hydrophilic zones (13). Here, as with the prior art systems as well as the systems shown in the first embodiment, particle cluster capsules which do not touch the surface (3) are not available to provide antimicrobial efficacy. On the other hand, despite the lower concentration of antimicrobial particles depicted in FIG. 3, the same or more antimicrobial actives are available for providing antimicrobial activity than depicted in either of FIG. 1 or 2. All of the particles (4) contained within the microcapsules (11) touching the surface (3) are available as a source of antimicrobial actives.

By the term hydrophilic, we mean water absorbing, water vapor adsorbing and wettable. By the term microcapsule, we mean the antimicrobial agent encapsulated with a hydrophilic polymer. Dependent upon the method used and the desired end use, individual particles of antimicrobial agent can be encapsulated (FIG. 2) or aggregates of particles of antimicrobial agent can be encapsulated (FIG. 3) to form microcapsules. Furthermore, the term encapsulate or the phrase encapsulated within contemplates that the antimicrobial agent is completely surrounded or encased by hydrophilic polymer as well as that it is substantially surrounded or encased by the hydrophilic polymer. As such, in the latter instance, the antimicrobial agent, in the form of a particle, may touch or protrude from the surface of the microcapsule or a surface of the antimicrobial agent, in the form of a particle, may form part of the surface of the microcapsule. For example, in the case of a flake, the flake may lie in the surface of the microcapsule, i.e., in the surface layer of the microcapsule, so that one entire face of the flake is in direct contact with the matrix polymer and not the encapsulating polymer.

Dependent upon the application, the rate of release can be tailored by proper selection of the hydrophilic polymer used as encapsulant in combination with the choice of the matrix polymer. The microcapsule should be dispersed in the matrix polymer, but remain as a second phase. Generally, the greater the water absorption of the hydrophilic polymer encapsulant, the greater the rate of release. For a polymer matrix that is highly hydrophilic, the rate of release can be slowed by choice of a hydrophilic polymer encapsulant with a lower water absorption than the matrix polymer.

Dependent upon the polymer and the processing conditions, prior art antimicrobial agents can cause discolorations. By use of the microcapsules of this invention, any discoloration due to the antimicrobial is primarily, if not completely, limited to the microcapsule and is not throughout the entire polymer matrix. Also, since less antimicrobial agent is necessary with the microcapsule, the extent of any discoloration is less and, thus, less of a problem.

The antimicrobial agent to be encapsulated contains a metal or metal ion that can impart antimicrobial activity. Examples of such metal ions include silver, copper, zinc, tin, gold, mercury, lead, iron, cobalt, nickel, manganese, arsenic, antimony, bismuth, barium, cadmium, chromium and thallium ions. Metal ions of silver, copper, zinc, and gold are preferred because they are considered safe for in vivo use. Silver ions are more preferred due to the fact that they have the highest ratio of efficacy to toxicity, i.e., high efficacy to low toxicity.

In addition to the metal or metal ion that imparts antimicrobial activity, optionally the antimicrobial agent may include or be used in conjunction with discoloration inhibiting agents and/or dopants. Preferred discoloration inhibiting agents include, but are not limited to inorganic discoloration inhibitors such as those of various ammonium salts. Dopants, which are particularly of use with the ion-exchange type antimicrobial agents, aid in the transport of the antimicrobial metal ion. These dopants provide a ready source of cations which exchange with and replace the antimicrobial silver metal ions in the ion-exchange ceramic particles, thereby facilitating release and transport of the silver ion. Preferred dopants include, but are not limited to inorganic salts of sodium such as sodium nitrate. For example, if sodium nitrate is used with a silver containing ion-exchange type antimicrobial agent, the sodium nitrate dissociates providing sodium ions which exchange with the antimicrobial silver ions, thereby releasing the silver ion for transport to the surface. In this example, the sodium nitrate expedites the release of the silver from the antimicrobial agent.

The antimicrobial agent can be in the form of a simple salt of the antimicrobial metal such as the oxide, sulfide, chloride, bromide, carbonate, nitrate, phosphate, dihydrogen phosphate, sulfate, oxalate, acetate, benzoate, thiosulfate and the like. Specific examples include silver nitrate, cupric oxide, zinc acetate and zinc oxide.

Alternatively, the antimicrobial agent may be in the form of a water soluble glass containing the antimicrobial agent or compound. Suitable antimicrobial water soluble glasses include those disclose in U.S. Pat. No. 5,470,585. By suitable adjustment of the glass composition, the dissolution rates in water can be controlled. Since their effectiveness requires dissolution in water, they are effective only at the surface where water may be present. The microcapsules of this invention, alleviates this problem since the hydrophilic polymer coating can enable water transport to the glass.

Preferably, the antimicrobial agent will be in the form of an ion-exchange type ceramic particle wherein antimicrobial metal ions have been exchanged for (replaced) other non-antimicrobially effective ions in the ceramic particles or a combination of the foregoing with an antimicrobial metal salt. Antimicrobial ceramic particles include, but are not limited to zeolites, hydroxyapatite, zirconium phosphates and other ion-exchange ceramics. Hydroxyapatite particles containing antimicrobial metals are described, e.g., in U.S. Pat. No. 5,009,898. Zirconium phosphates containing antimicrobial metals are described, e.g., in U.S. Pat. Nos. 5,296,238; 5,441,717 and 5,405,644. Because of the two dimensional network structure of zirconium phosphates, delivery of the antimicrobial metal to the surface can be especially difficult. In a zirconium phosphate type particle, the antimicrobial actives are present between sheets of the zirconium phosphate and the passage of the antimicrobial metal ions is limited to the x and y directions defining the space between the sheet, not in the z direction through the sheets themselves. In essence, the zirconium phosphate particle is like an Oreo cookie where the antimicrobial agent is present in the filling. The point of release is at the edges open to the filling, not through the cookies. It is believed that this phenomenon results in somewhat lower efficacy for the zirconium phosphates versus those ion-exchange type antimicrobial particles which release three dimensionally. In this case even zirconium phosphate particles which touch the surface but do not have an open edge touching the surface would not be available to release antimicrobial metal ions. Thus, the use of microcapsules of this invention alleviates this problem since the metal can be transported through the hydrophilic encapsulant to the surface of the matrix. More preferably, antimicrobial zeolite is employed containing ion-exchanged antimicrobial metal ions.

In antimicrobial zeolite particles used in the preferred embodiment of the present invention, ion-exchangeable ions present in zeolite, such as sodium ions, calcium ions, potassium ions and iron ions are partially replaced with antimicrobial metal ions. Optionally, other ions may also be exchanged for better efficacy and/or color stability, including ammonium ions. Such ions may co-exist in the antimicrobial zeolite particle since they do not prevent the bactericidal effect. Examples of antimicrobial metal ions include, but are not limited to, ions of silver, copper, zinc, gold, mercury, tin, lead, bismuth, cadmium, chromium and thallium. Preferably, the antimicrobial metal ions are silver, copper or zinc ions, and most preferably silver is employed. These antimicrobial metal ions may be incorporated into the zeolite by themselves or in a mixture, for example mixtures of silver and zinc ions or mixtures of silver and copper ions.

The antimicrobial metal ion is present in the range of from about 0.1 to about 25 wt % of the zeolite based upon 100% total weight of zeolite. Preferably, the antimicrobial metal ion is present in the range of from about 0.3 to about 20 wt % of the zeolite based upon 100% total weight of zeolite. Most preferably, the antimicrobial metal ion is present in the range of from about 2 to about 10 wt % of the zeolite based upon 100% total weight of zeolite. In one embodiment, the zeolite contains from about 0.1 to about 15 wt % of silver ions and from about 0.1 to about 15 wt % of copper and/or zinc ions. Although ammonium ion may be contained in the zeolite at a concentration as high as about 20 wt % of the zeolite, it is desirable to limit the content of ammonium ions to about 0.5 to about 2.5 wt % of the zeolite, more preferably from about 0.5 to about 2.0 wt %, and most preferably, from 0.5 to about 1.5 wt %.

Antimicrobial zeolites, including the antimicrobial zeolites disclosed in U.S. Pat. No. 4,911,898; 4,911,899 and 4,938,958, are well known and may be prepared for use in the present invention using known methods.

Either natural zeolites or synthetic zeolites may be used to prepare the antimicrobial zeolites used in the present invention. "Zeolite" is an aluminosilicate having a three dimensional skeletal structure that is represented by the formula: $XM_{2/n}O$—$Al_2O_3$—$YSiO_2$-$ZH_2O$. M represents an ion-exchangeable ion, generally a monovalent or divalent metal ion; n represents the atomic valency of the (metal) ion; X and Y represent coefficients of metal oxide and silica, respectively; and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. The present invention is not restricted to use of these specific zeolites.

The ion-exchange capacities of these zeolites are as follows: A-type zeolite=7 meq/g; X-type zeolite=6.4 meq/g; Y-type zeolite=5 meq/g; T-type zeolite=3.4 meq/g; sodalite=11.5 meq/g; mordenite=2.6 meq/g; analcite =5 meq/g; clinoptilolite=2.6 meq/g; chabazite=5 meq/g; and erionite=3.8 meq/g. These ion-exchange capacities are sufficient for the zeolites to undergo ion-exchange with ammonium and antimicrobial metal ions.

The specific surface area of preferred zeolite particles is preferably at least 150 m$^2$/g (anhydrous zeolite as standard) and the $SiO_2/Al_2O_3$ mole ratio in the zeolite composition is preferably less than 14 and more preferably less than 11.

The antimicrobial metal ions used in the antimicrobial zeolites should be retained on the zeolite particles through an ion-exchange reaction. Antimicrobial zeolites in which the antimicrobial metal ions are adsorbed or attached without an ion-exchange reaction typically exhibit an overall decreased bactericidal effect and their antimicrobial effect is not long-lasting. Nevertheless, it can be advantageous for imparting quick antimicrobial action to maintain a sufficient amount of surface adsorbed metal ion in addition to the ion-exchanged metal ion.

The antimicrobial zeolites, as well as other antimicrobial ceramic particles, may also contain a discoloration agent. Preferably, the discoloration agent is biocompatible. Preferred discoloration agents include, but are not limited to, inorganic discoloration inhibitors such as ammonium. More preferably, the inorganic discoloration inhibitor is an ion-exchanged ammonium ion in the zeolite.

A preferred antimicrobial zeolite for use in the invention is type A zeolite containing a combination of ion-exchanged silver, zinc, copper, and ammonium; silver copper and ammonium or silver and ammonium. One such zeolite is distributed by AgION Technologies, L.L.C. under the product number AW-10N and consists of 0.6% by weight of silver ion-exchanged in Type A zeolite particles having a mean average diameter of about 3µ. Another grade, AJ-10N, consists of about 2% by weight of silver ion-exchanged in Type A zeolite particles having a mean average diameter of about 3µ. Yet another grade, AW-80, contains 0.6% by weight of silver ion-exchanged in Type A zeolite particles having a mean average diameter of about 2µ. Another grade, AJ-80N, consists of about 2% by weight of silver ion-exchanged in Type A zeolite particles having a mean average diameter of about 1µ. These specific zeolites typically contain about 14% by weight zinc in combination with between about 0.5% and 2.5% by weight of ion-exchanged ammonium as a discoloration inhibiting agent.

The hydrophilic polymer used to encapsulate the antimicrobial agent is a polymer that can absorb sufficient water to enable the encapsulated particle to exhibit good antimicrobial behavior, i.e., to allow for the migration and release of the antimicrobial active agent. The polymer will be characterized by having water absorption at equilibrium of at least about 2% by weight measured by ASTM D570. Preferably, the polymer will have water absorption at equilibrium of at least about 5 % by weight. More preferably, the polymer will have water absorption at equilibrium of at least about 20% by weight. Especially suitable hydrophilic polymers include those having water contents of from about 50 and to about 150% by weight.

Polymeric compositions for use as the encapsulant in the present invention include polymers, which are comprised of substantial quantities of monomers having polar groups associated with them, such that the overall polymeric composition is rendered hydrophilic. The polar groups can be incorporated into the polymer main chain as in for example polyesters, polyurethanes, polyethers or polyamides. Optionally the polar groups can be pendant to the main chain as in for example, polyvinyl alcohol, polyacrylic acids or as in ionomers such as Surlyn®. Surlyn® is available from Dupont and is the random copolymer poly(ethylene-co-methacrylic acid) wherein some or all of the methacrylic acid units are neutralized with a suitable cation, commonly Na$^+$ or Zn$^{+2}$. While not being limited by way of theory, it is believed that the inclusion of polar groups allows water to more readily permeate the polymer and consequently, to allow slow transport of the metal ion through the encapsulating polymer layer.

A number of hydrophilic polymers may be used in the present invention and include, for example, (poly)hydroxyethyl methacrylate, (poly)hydroxypropyl methacrylate, (poly)glycerol methacrylate, copolymers of hydroxyethyl methacrylate and methacrylic acid, polyacrylamide, hyaluronan, polysaccharides, polylactic acid, copolymers of lactic acid, (poly)vinyl pyrrolidone, polyamides such as Nylon 6,6 or Nylon 4,6 or Nylon 6,12, cellulosics, polyureas, polyurethanes and certain polyesters containing a high percentage (at least about 10% by weight, preferably at least about 25% by weight or more) of polyalkylene oxide.

The hydrophilic polymer may be a copolymer containing at least a substantial amount of at least one or more of the above-mentioned hydrophilic monomers, including, for example, styrene/methacrylic acid/hydroxyethyl methacrylate copolymers, styrene/methacrylic acid/hydroxypropyl methacrylate copolymers, methylmethacrylate/methacrylic acid copolymers, ethyl methacrylate/styrene/methacrylic acid copolymers and ethyl methacrylate/methyl methacrylate/styrene/methacrylic acid copolymers, copolymers based upon the cellulosics, and copolymers which utilize vinylpyrrolidone monomers, among numerous others.

Other hydrophilic polymers that may be used in the present invention include polyvinyl acetate, polyvinyl alcohol, and copolymers of polyvinyl alcohol and polyvinylacetate, polyvinylchloride, copolymers of polyvinylacetate and polyvinylchloride and hydroxyl-modified vinyl chloride/vinyl acetate copolymers.

Polyurethanes containing a high percentage (at least about 10% by weight, preferably at least about 25% by weight or more) of polyalkylene oxide are especially useful in this invention.

Preferably the hydrophilic polymer is chosen from polyhydroxyethyl methacrylate, polyacrylamide, polyvinylpyrrolidinone, polyurea, polysaccharides, polylactic acid and polyurethane. More preferably, the hydrophilic polymer is hydrophilic polyurethane, such as the TECOPHILIC® polyurethane sold by Thermedics of Woburn, Mass.

In the case of individually encapsulated antimicrobial particles, the microcapsule has a coating thickness of up to 15µ of hydrophilic polymer on the antimicrobial agent, preferably a coating thickness of 1 to 10µ. Thicker coatings could be used efficaciously; however, concern must then be given to the impact, if any, of the presence of the hydrophilic polymer on the properties of the matrix resin into which the encapsulated particles are to be incorporated.

In the case of microcapsules containing multiple antimicrobial particles, especially of the ion-exchange type, the microcapsules may have a mean average diameter of up to and over 2000µ, but not likely over 3000µ. Generally the microcapsules will have a mean average diameter of from about 15 to about 1000µ, preferably from about 50 to about 300µ, most preferably from about 90 to about 200µ. Of course smaller or larger microcapsules can be used. However, the smaller the microcapsule the more closely one approaches a system of individually encapsulated particles. Similarly, the larger the particles, the more potential there is for a deleterious effect on the physical properties of the polymer matrix and the greater the distance between particles at the surface, in the case of equivalent weights of larger versus small particle size microcapsules. Of course, microcapsule size and shape is somewhat dependent upon the size and shape of the antimicrobial particles to be incorporated therein as well as the process by which the microcapsules are made.

Typically the microcapsules made in accordance with the present invention will be of a generally spherical or elliptical shape, although other shapes such as flakes and fibers are also contemplated. Generally the aspect ratio of these microcapsules will be from 1 to about 4, preferably from 1 to about 2, most preferably from 1 to about 1.5. Depending upon the method of manufacture, in most instances the aspect ration will be about 1. As used herein, the term aspect ratio refers to the quotient of the largest dimension divided by the smallest dimension of the particle: the largest dimension being the mean average diameter of the particle in the case of spherical/-elliptical particles and, vice-versa, the mean average diameter being the largest dimension in the case of non-spherical and non-elliptical particles. As disclosed in applicants co-filed application entitled "High Aspect Ratio Encapsulated Inorganic Antimicrobial Additive for Controlled Release", high aspect ratio microcapsules, those up to 100 or more, but typically up to 30, are also useful and provide certain added benefits, in certain applications, as compared to the lower aspect ratios within the ranges set forth above.

The microcapsule may be prepared by dissolving the hydrophilic polymer in a suitable solvent. Preferably this is done to make a solution that contains from about 1% to about 75% by weight of the hydrophilic polymer. More preferably, the solution contains from about 2% to about 40% by weight of the hydrophilic polymer and most preferably, the solution contains from about 5% to about 30% by weight of the hydrophilic polymer. Solutions that are more dilute than 1%, while useful in this invention, require handling larger levels of solvent. Solutions that are more concentrated than about 75% often are quite viscous and present some difficulties in handling.

The choice of solvent will vary based upon the particular hydrophilic polymer as well as the end use application for the antimicrobial composition. It should be a solvent or solvent mixture that dissolves the hydrophilic polymer and one in which the antibacterial agent is mainly insoluble. For those applications in which residual solvents can pose problems, efforts should be taken to select more compatible or appropriate solvents and/or ensure that the solvent is completely driven from the microcapsules. Preferred solvents include tetrahydrofuran, dimethylacetamide, methylethylketone, and mixtures thereof.

The antimicrobial agent is added to the solution of the hydrophilic polymer, preferably with agitation. The amount of antimicrobial agent can be varied. Preferably the antimicrobial agent is added at 1 to 1000 parts by weight per 100 parts by weight of the hydrophilic polymer. More preferably, the antimicrobial agent is added at 10 to 200 parts by weight per 100 parts by weight of the hydrophilic polymer. Most preferably, the antimicrobial agent is added at 20 to 100 parts by weight per 100 parts by weight of the hydrophilic polymer. If the amount of antimicrobial agent added is too low, then the resultant microcapsules may have lower and shorter lived antimicrobial activity. If the amount of antimicrobial agent added is too high, then the resultant microcapsules will not have good dispersion capabilities. Of course the level of incorporation is dependent upon whether the individual antimicrobial particles are to be encapsulated or microcapsules containing multiple antimicrobial particles are to be prepared. Additional factors affecting the level of incorporation include the particle size of the antimicrobial agent and the "loading capacity" of the hydrophilic polymer encapsulant. By loading capacity is meant the ability of the polymer to incorporate the antimicrobial particles without compromising too much the integrity of the microcapsule, i.e., there must be sufficient hydrophilic polymer to create a microcapsule. Generally speaking, these same factors and considerations pertain to all methods for the preparation of the microcapsules according to the present invention.

This mixture of the antimicrobial agent in the hydrophilic polymer solution is then added to an antisolvent, preferably with agitation, to precipitate the microcapsules. The antisolvent is a solvent or solvent mixture that is miscible with the solvent chosen to dissolve the polymer. Further the antisolvent is chosen such that the hydrophilic polymer is substantially insoluble in the antisolvent. It is preferable that the antisolvent has a boiling point below 150° C. so that residual amounts can be easily removed from the microcapsule by drying. The amount of antisolvent can vary, but should be enough to precipitate the microcapsules. Preferably the amount of antisolvent used is from 50 to 2000 parts based upon 100 parts of solvent. Smaller amounts are often insufficient. Larger amounts are not necessary and add to the cost.

The microcapsules are separated from the liquid and dried. The drying temperature is chosen such that it is low enough to have little affect on the hydrophilic polymer and high enough to remove residual solvent. The particular conditions will vary based upon the polymer, but temperatures from 20-100° C. are common. Optionally, vacuum may be employed in the drying step.

By varying the precipitation conditions such as stirring speed, rate of precipitation, choice of antisolvent and amount of antisolvent, individually encapsulated particles as well as microcapsules having a varied amount of individual particles and/or agglomerates of particles within the encapsulant can be prepared. Optimum conditions will vary dependent upon the particular antimicrobial agent used, the hydrophilic polymer and the desired end use. Of course, in the solvent processing methodology, the selection of solvent and antisolvent must be such as not to adversely affect the efficacy of the antimicrobial agent.

Alternatively, the microcapsules may be prepared by treating the antimicrobial agent with a polymer precursor and then subsequent polymerization to prepare the hydrophilic polymer. In this embodiment, the antimicrobial agent is mixed with a polymer precursor, optionally with a solvent, to obtain an antimicrobial agent coated with the polymer precursor. The polymer precursor can be a simple polymer precursor such as ethylene glycol, hydroxyethylmethacrylate or 1,6-diaminohexane. Preferably the polymer precursor is oligomeric or polymeric such as a polyol, polyamine, polyether diol, polyether diamine or polyalcohol amine. The subsequent polymerization can be effected by treatment with a reactive ingredient such as a diisocyanate. The subsequent polymerization can be done by different techniques. One preferred method involves suspension of the antimicrobial agent coated with the polymer precursor in a fluidized bed and addition of a reactive ingredient such as a diisocyanate. By varying the reaction conditions such as stirring speed, temperature, and choice of polymer precursors, individually encapsulated particles as well as microcapsules having a varied amount of individual particles and/or agglomerates of particles within the encapsulant can be prepared. Optimum conditions will vary dependent upon the particular antimicrobial agent used, the hydrophilic polymer and the desired end use.

Another method for preparation of the microcapsules is the compounding of the antimicrobial agent with the hydrophilic polymer and subsequent grinding of the compounded product to the desired particle size. This can be done by mixing the antimicrobial agent with the hydrophilic polymer to obtain a blend. The blend is then melt compounded to obtain solid particles, which can then be ground to give the microcapsules. The melt compounding can be done by several methods such as with an extruder or kneader to yield a compounded product, preferably in the form of pellets. The optimum conditions will vary based upon the choice of the hydrophilic polymer. The compounded product can be ground to give the microcapsules of the desired particle size. Preferably, the microcapsule has a mean average particle size of 15 to 1000μ, more preferably an average particle size of 50-300 μ, most preferably an average particle size of 90-200μ. This method tends to give agglomerates of antimicrobial agent encapsulated with the hydrophilic polymer as the microcapsules. Dependent upon the hydrophilic polymer, it may be preferable to cryogenically grind the compounded product.

The amount of antimicrobial agent encapsulated with the hydrophilic polymer is an amount that is effective to form a microcapsule with good antimicrobial activity. The microcapsules preferably contains from about 1 to about 1000 parts by weight of antimicrobial agent per 100 parts by weight of hydrophilic polymer. More preferably, the microcapsules contain from about 10 to about 200 parts by weight of antimicrobial agent per 100 parts by weight of hydrophilic polymer and, most preferably, from about 20 to about 100 parts by weight of antimicrobial agent per 100 parts by weight of hydrophilic polymer.

The microcapsules can be used to impart antimicrobial properties to a variety of compositions. They may be blended into various formulations to provide compositions useful for molding, coatings or films with antimicrobial activity. They are particularly useful when blended with polymer formulations to provide compositions useful for molding articles with antimicrobial properties. The combination of hydrophilic polymer encapsulant and matrix polymer should be such that they have a different level of hydrophilicity and such that the microcapsule remains as a second phase in the matrix polymer. The matrix polymer formulations may be based upon either hydrophilic or non-hydrophilic polymers including, but not limited to: polypropylene, polyethylene, polystyrene, ABS, SAN, polybutylene terephthalate, polyethylene terephthalate, nylon 6, nylon 6,6, nylon 4,6, nylon 12, phenolic resins, urea resins, epoxy resins, polyvinylchloride, polyurethanes, silicone polymers, polycarbonates, polyphenylene ethers, polyamides, polyethylene vinylacetate, polyethylene ethyl acrylate, polylactic acid, polysaccharides, polytetrafluoroethylene, polyimides, polysulfones, and a variety of other polymers and copolymers.

The antimicrobial polymer and polymer coating compositions made in accordance with the practice of the present invention may be used in any applications where antimicrobial properties are desirable. Exemplary applications include cutting boards, catheters and other medical devices, pipes, containers, toothbrushes, diapers, air filters, appliances, conveying belts, bottles, liquid dispensers, faucets, humidifiers, air conditioners, mats, razors, and bandages. Coatings comprising the microcapsule may be in liquid or solution form or may be in the form of a powder coating. In the latter instance, the microcapsule may be dry blended with another polymer resin powder which is then used to powder coat a substrate.

The antimicrobial properties of the articles made from the microcapsules of the invention show efficacy for the end use applications. The degree of efficacy may be determined by any of several tests such as the Dow shaker test, direct inoculation and several others known to those skilled in the art and chosen based upon the end use application.

The present invention will hereunder be explained in more detail with reference to the following non-limiting working examples.

EXAMPLES

Comparative Example 1

For comparative purposes, a polymer blend was made by first compounding an antimicrobial agent with a nonhydrophilic polymer and then using that mixture in a polymer formulation. Twenty parts by weight of AgION AJ10D (about 2.5% by weight of silver ion-exchanged in Type A zeolite particles having a mean average diameter of about 3.) was gravimetrically fed with 80 parts by weight of LDPE resin, extruded, pelletized and ground to give particles. A mixture of 25 parts by weight of these particles combined with 75 parts by weight of LDPE was blended by shaking and injection molded into 5 cm by 5 cm by 0.16 cm test parts. The injection molding temperature conditions were 385° F. rear zone; 390° F. front zone and 395° F. nozzle temperature. Analysis of the test parts was done in duplicate by ashing the sample and showed a measured loading of AgION powder of 4.8% and 4.5% by weight. No other inorganic materials were present in the sample.

Example 2

A polymer blend was made by first compounding an antimicrobial agent with a hydrophilic polymer and then using the microcapsule in a polymer formulation. Fifty parts by weight of AgION AJ10D (about 2.5% by weight of silver ion-exchanged in Type A zeolite particles having a mean average diameter of about 3μ.) was gravimetrically fed with 50 parts by weight of Tecophilic® 60 resin, a hydrophilic polyurethane available from Thermedics Inc. having a moisture absorption of about 60%. The blend was extruded using a Leistritz 27 mm twin screw extruder, pelletized, dried and cryogenically ground. Sieving was performed with a 100 mesh screen to remove large particles. SEM analysis of the resultant microcapsules showed particles that were roughly equiaxed and below about 150μ in size. A mixture of 4 parts by weight of microcapsule was combined with 96 parts by weight of LDPE was blended by shaking and injection molded into 5 cm by 5 cm by 0.16 test parts. The injection molding temperature conditions were 385° F. rear zone; 390° F. front zone and 395° F. nozzle temperature. Analysis of the test parts was done in duplicate by ashing the sample and showed a measured loading of AgION powder of 2.3% and 2.3% by weight. No other inorganic materials were present in the sample.

Example 3

The procedure of example 2 was repeated, but with a mixture of 10 parts by weight of microcapsule and 90 parts by weight of LDPE. Analysis of the test parts was done in duplicate and showed a measured loading of AgION powder of 5.4% and 5.2% by weight. No other inorganic materials were present in the sample.

Extraction experiments were performed on the test parts from examples 1-3 to determine the total amount of silver accessible from the samples. This was accomplished using the basic approach of serial extraction. The method involves placing the samples in a test solution and changing it periodically, measuring the volume and Ag concentration each time to determine the amount of silver removed with each cycle. The extraction experiment was performed in duplicate so six samples total were tested. The samples were placed in plastic beakers containing 40 ml of extraction solution (0.8% NaNO3). To keep the samples from floating and only contacting the solution on one side, the beakers were crimped from the sides, pinning the coupons to the bottom of the beaker. To ensure even release, the beakers were placed on a rocking table to agitate during the release time. The samples soaked for at least 24 hours between solution changes.

The results are in Table 1.

TABLE 1

Extraction of Test Parts.
Comparative Example 1, Example 2 and Example 3 in duplicate.
Measurements Expressed in micrograms of silver extracted.

| Extraction | C1 | C1d | Mean | E2 | E2d | Mean | E3 | E3d | Mean |
|---|---|---|---|---|---|---|---|---|---|
| 1 | 8.5 | 7.4 | 7.9 | 7.5 | 7.0 | 7.2 | 14.4 | 11.8 | 13.1 |
| 2 | 0.7 | 0.7 | 0.7 | 1.2 | 1.4 | 1.3 | 4.0 | 3.1 | 3.6 |
| 3 | 0.2 | 0.2 | 0.2 | 1.2 | 1.4 | 1.3 | 3.6 | 2.5 | 3.1 |
| 4 | 0.1 | 0.1 | 0.1 | 0.3 | 0.4 | 0.4 | 2.0 | 1.4 | 1.7 |
| 5 | 0.0 | 0.0 | 0.0 | 0.2 | 0.3 | 0.2 | 0.7 | 0.5 | 0.6 |
| 6 | 0.0 | 0.0 | 0.0 | 0.2 | 0.2 | 0.2 | 0.4 | 0.4 | 0.4 |
| 7 | 0.0 | 0.0 | 0.0 | 0.8 | 0.4 | 0.6 | 1.1 | 0.4 | 0.7 |
| 8 | 0.0 | 0.0 | 0.0 | 0.2 | 0.2 | 0.2 | 0.5 | 0.4 | 0.5 |

TABLE 1-continued

Extraction of Test Parts.
Comparative Example 1, Example 2 and Example 3 in duplicate.
Measurements Expressed in micrograms of silver extracted.

| Extraction | C1 | C1d | Mean | E2 | E2d | Mean | E3 | E3d | Mean |
|---|---|---|---|---|---|---|---|---|---|
| 9 | 0.0 | 0.0 | 0.0 | 0.2 | 0.2 | 0.2 | 1.0 | 0.6 | 0.8 |
| 10 | 0.0 | 0.0 | 0.0 | 0.2 | 0.3 | 0.2 | 0.7 | 0.4 | 0.6 |
| 11 | 0.0 | 0.0 | 0.0 | 0.1 | 0.1 | 0.1 | 0.3 | 0.2 | 0.3 |
| 12 | 0.0 | 0.0 | 0.0 | 0.1 | 0.1 | 0.1 | 0.2 | 0.2 | 0.2 |
| Total | 9.4 | 8.4 | 8.9 | 12.3 | 12.0 | 12.1 | 28.9 | 22.1 | 25.5 |

As can be seen by inspection of Table 1, the formulation of Example 2 delivers more silver (12.1 micrograms on average) than the formulation of Comparative Example 1 (8.9 micrograms on average). This is true despite the fact that the formulation of Example 2 has about half of the loading of antimicrobial agent. Example 3 delivers remarkably more (25.5 micrograms) silver than the formulation of Comparative Example 1 (8.9 micrograms). This is true despite the fact that they have similar loadings of antimicrobial agent. That half the loading gives slightly more silver and therefore slightly better antimicrobial activity and that similar loadings give remarkably greater silver and therefore remarkably greater antimicrobial activity is unexpected and shows the advantage of using microcapsules.

Note also that after the fourth extraction, no appreciable amount of silver is available from Comparative Example 1, whereas the formulations of the invention continue to deliver silver and therefore antimicrobial activity even after eleven extractions. This shows the ability of formulations of the invention to impart sustained antimicrobial activity long after prior art inventions are inactive.

Comparative Example 4

A test part was prepared as in Comparative Example 1. Analysis by ashing the sample showed a powder loading of 5.0% by weight. No other inorganic materials were present in the sample. The surface was analyzed for surface exposure on the SEM using image analysis. The voltage used was 10 keV, chosen to detect only the immediate surface particles. Ten measurements were done and averaged to give a value of 0.9% by area of powder at the surface.

Example 5

A test part was prepared as in Example 3. Analysis by ashing the sample showed a powder loading of 4.8%. No other inorganic materials were present in the sample. The surface was analyzed as in Comparative Example 4 and an average value of 1.3% by area of powder at the surface was obtained. This result shows that the article has a higher level of antimicrobial agent at the surface, where it is needed, than the prior art formulation of Comparative Example 4, despite the fact that the overall loading is the same.

Example 5 also demonstrates another beneficial and surprising phenomenon of the present invention which is manifested by an enhancement in the amount of antimicrobial agent at the surface of parts molded from polymer compositions containing the microcapsules made in accordance with the teaching of the present invention. Specifically, by controlled selection of the hydrophilic polymer encapsulant and matrix polymer as well as the processing conditions for molding parts from such a formulation, one is able to generate a smearing of the microcapsule along the surface of the molded part. It is believed that by selecting a polymer matrix resin whose processing temperature is near, at or above, preferably at or above, the temperature at which the hydrophilic polymer begins to manifest tackiness or plastic deformation, microcapsules which, upon injection into the mold, touch the surface of the mold, adhere to the surface and, as the flow of matrix resin continues to fill the mold, is pulled along the surface of the mold, smearing the microcapsule at the part surface. This same phenomenon is also believed to manifest itself when the mold surface temperatures are near, at or above, preferably at or above, the temperature at which the hydrophilic polymer begins to manifest tackiness or plastic deformation.

Thus the microcapsules of the invention are exceptionally suitable for use in various compositions and provide compositions without the deleterious effects of the prior art.

While preferred embodiments of the invention have been described in the foregoing examples, it will be understood by those skilled in the art that various changes and modifications may be made therein without departing from the spirit and the scope of the invention. Accordingly, the above description should be construed as illustrating and not limiting the scope of the invention.

What is claimed is:

1. A polymer composition comprising a) an antimicrobial additive comprising 10 to 1000 parts by weight of at least one ion-exchange type antimicrobial agent comprising a ceramic carrier and ion-exchanged antimicrobial metal ions and 100 parts by weight of a water absorbing, water vapor absorbing and wettable hydrophilic polymer having a water absorption at equilibrium of at least 5% by weight, the extent of water absorption being sufficient to allow for ion transport within and through, the hydrophilic polymer so as to facilitate the ion-exchange and subsequent release of an antimicrobially effective amount of the antimicrobial metal ions, said antimicrobial additive in the form of microparticles of the hydrophilic polymer having dispersed therein multiple particles of the at least one ion-exchange type antimicrobial agent, said microparticles having an average diameter of from about 15μ to about 300μ; and b) a matrix polymer wherein the hydrophilic microparticles are dispersed as a discrete phase within the matrix polymer.

2. The polymer composition according to claim 1 wherein the antimicrobial agent is a zeolite that contains silver ions alone or in combination with zinc ions or copper ions or both.

3. The polymer composition according to claim 1 wherein the hydrophilic polymer is a polymer with water absorption at equilibrium of at least about 20% by weight.

4. The polymer composition according to claim 1 wherein the hydrophilic polymer is selected from the group consisting of polyhydroxyethyl methacrylate, polyacrylamide, N-vinyl-2-pyrrolidinone, polysaccharides, polylactic acid, polyamide and polyurethane.

5. The polymer composition according to claim 1 wherein the hydrophilic polymer is polyurethane.

6. The polymer composition according to claim 1 wherein the microparticles contain from 10 to 200 parts by weight of antimicrobial agent based upon 100 parts by weight of hydrophilic polymer.

7. The polymer composition according to claim 1 wherein the microparticles contain from 20 to 100 parts by weight of antimicrobial agent based upon 100 parts by weight of hydrophilic polymer.

8. The polymer composition according to claim 1 further comprises an inorganic discoloration inhibiting agent.

9. The polymer composition according to claim 8 wherein said discoloration inhibiting agent is an ammonium compound.

10. The polymer composition according to claim 8 wherein the inorganic discoloration inhibiting agent comprises ion-exchanged ammonium ions contained within said antimicrobial agent.

11. The polymer composition according to claim 1 further comprising a dopant agent.

12. The polymer composition according to claim 11, wherein said dopant is an inorganic sodium salt.

13. The polymer composition according to claim 12, wherein said dopant is sodium nitrate.

14. The polymer composition of claim 1 wherein the matrix polymer is an addition polymer selected from the group consisting of polypropylene, polyethylene, polystyrene, polyvinylchloride, ABS, SAN, epoxy resins and polytetrafluoroethylene.

15. The polymer composition of claim 1 wherein the matrix polymer is a condensation polymer selected from the group consisting of polyurethanes, polycarbonates, polyesters, polyamides, polyimides and silicone polymers.

16. The polymer composition of claim 1 wherein the matrix polymer is not a hydrophilic polymer.

17. The polymer composition of claim 1 wherein the matrix polymer is a hydrophilic polymer whose hydrophilic property is different from that of the hydrophilic polymer used to make the antimicrobial hydrophilic polymer microparticle.

18. The polymer composition of claim 1 wherein the matrix polymer is a polymer blend.

19. The polymer composition according to claim 1 wherein the mean average diameter is from about 15μ to about 200μ.

20. The polymer composition according to claim 1 wherein the mean average diameter is from about 50μ to about 200μ.

21. The polymer composition according to claim 1 wherein the antimicrobial agent comprises a ceramic carrier selected from the group consisting of zeolites, hydroxyapatites and zirconium phosphates having ion-exchanged antimicrobial metal ions.

22. The polymer composition according to claim 1 wherein the antimicrobial metal ion is selected from the group consisting of silver, copper, zinc, tin, gold, mercury, lead, iron, cobalt, nickel, manganese, arsenic, antimony, bismuth, barium, cadmium, chromium, thallium and combinations thereof.

23. The polymer composition according to claim 1 wherein the antimicrobial metal ion is silver, zinc, copper or a combination of any two or all three of the foregoing.

24. A polymer composition comprising a) an antimicrobial additive comprising a discrete particle of an ion-exchange type antimicrobial agent comprising a ceramic carrier and ion-exchanged antimicrobial metal ions encapsulated in a water absorbing, water vapor absorbing and wettable hydrophilic polymer having a water absorption at equilibrium of at least 5% by weight and sufficient to allow for ion transport within and through the hydrophilic polymer so as to facilitate the ion-exchange and subsequent release of an antimicrobially effective amount of the antimicrobial metal ions, the thickness of the hydrophilic polymer coating being from about 1μ to about 15μ, said antimicrobial additive having a mean average particle size of about 300μ or less and a weight ratio of the antimicrobial agent to the hydrophilic polymer of from 1:100 to 1000:100 and b)

a matrix polymer wherein the antimicrobial additive particles are dispersed as a discrete phase within the matrix polymer.

25. The polymer composition according to claim 24 wherein the antimicrobial agent is coated with the hydrophilic polymer and the coating has a thickness of 1μ to 10μ.

26. The polymer composition according to claim 24 wherein the hydrophilic polymer is polyurethane.

27. The polymer composition according to claim 24 wherein the ceramic carrier is selected from the group consisting of zeolites, hydroxyapatites, and zirconium phosphates.

28. The polymer composition according to claim 24 wherein the antimicrobial metal ion is selected from the group consisting of silver, copper, zinc, tin, gold, mercury, lead, iron, cobalt, nickel, manganese, arsenic, antimony, bismuth, barium cadmium, chromium, thallium and combinations thereof.

29. The polymer composition according to claim 24 wherein the antimicrobial metal ion is silver, zinc, copper or a combination of any two or all three of the foregoing.

30. The polymer composition according to claim 24 wherein the antimicrobial agent is a zeolite that contains silver ions alone or in combination with zinc ions or copper ions or both.

31. The polymer composition according to claim 24 wherein the hydrophilic polymer is a polymer with water absorption at equilibrium of at least about 20% by weight.

32. The polymer composition according to claim 24 wherein the hydrophilic polymer is selected from the group consisting of polyhydroxyethyl methacrylate, polyacrylamide, N-vinyl-2-pyrrolidinone, polysaccharides, polylactic acid, polyamide and polyurethane.

33. The polymer composition of claim 24 wherein the matrix polymer is an addition polymer selected from the group consisting of polypropylene, polyethylene, polystyrene, polyvinylchloride, ABS, SAN, epoxy resins and polytetrafluoroethylene.

34. The polymer composition of claim 24 wherein the matrix polymer is a condensation polymer selected from the group consisting of polyurethanes, polycarbonates, polyesters, polyamides, polyimides and silicone polymers.

35. The polymer composition of claim 24 wherein the matrix polymer is a hydrophilic polymer whose hydrophilic property is different from that of the hydrophilic polymer encapsulant used to make the microcapsule.

36. The polymer composition according to claim 24 further comprises an inorganic discoloration inhibiting agent.

37. The polymer composition according to claim 36 wherein said discoloration inhibiting agent is an ammonium compound.

38. The polymer composition according to claim 36 wherein the inorganic discoloration inhibiting agent comprises ion-exchanged ammonium ions contained within said antimicrobial agent.

39. The polymer composition according to claim 24 further comprising a dopant agent.

40. The polymer composition according to claim 39 wherein said dopant is an inorganic sodium salt.

41. The polymer composition according to claim 40 wherein said dopant is sodium nitrate.

42. The polymer composition of claim 24 wherein the matrix polymer is a hydrophilic polymer whose hydrophilic property is different from that of the hydrophilic polymer used to make the antimicrobial hydrophilic polymer microparticle.

43. The polymer composition of claim 24 wherein the matrix polymer is a polymer blend.

\* \* \* \* \*